(12) United States Patent
Fuhrman et al.

(10) Patent No.: US 6,591,836 B1
(45) Date of Patent: Jul. 15, 2003

(54) DEVICE AND METHOD OF REDUCING BIAS FLOW IN OSCILLATORY VENTILATORS

(75) Inventors: Bradley P. Fuhrman, Buffalo, NY (US); Mark S. Dowhy, Buffalo, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 09/631,464

(22) Filed: Aug. 3, 2000

Related U.S. Application Data
(60) Provisional application No. 60/146,863, filed on Aug. 3, 1999.

(51) Int. Cl.[7] ............................................. A62B 9/02
(52) U.S. Cl. ........................ 128/205.24; 128/205.28; 128/207.16
(58) Field of Search .................... 128/200.14, 200.24, 128/201.2 S, 201.28, 203.12, 203.15, 204.18, 204.21, 204.23, 204.26, 205.24 OR, 205.28, 207.14, 207.16, 207.18

(56) References Cited

U.S. PATENT DOCUMENTS

| | | | | |
|---|---|---|---|---|
| 4,466,433 A | | 8/1984 | Robbins ................ | 128/202.22 |
| 4,543,951 A | * | 10/1985 | Phuc .................... | 128/204.25 |
| 4,719,910 A | | 1/1988 | Jensen ................... | 128/204.21 |
| 4,747,402 A | | 5/1988 | Reese et al. ........... | 128/204.21 |
| 4,805,612 A | | 2/1989 | Jensen ................... | 128/204.21 |
| 4,821,709 A | * | 4/1989 | Jensen ................... | 128/204.21 |
| 4,879,996 A | * | 11/1989 | Harwood et al. ...... | 128/202.26 |
| 5,092,326 A | | 3/1992 | Winn et al. ............ | 128/250.13 |
| 5,165,398 A | | 11/1992 | Bird ...................... | 128/204.25 |
| 5,307,794 A | | 5/1994 | Rauterkus et al. ..... | 128/204.18 |
| 5,555,880 A | * | 9/1996 | Winter et al. .......... | 128/204.21 |
| 5,850,835 A | | 12/1998 | Takaki et al. .......... | 128/204.18 |

OTHER PUBLICATIONS

Intrapulmonaler Gaswechsel unter simulierter Apnoe durch transtrachealen, periodischen intrathorakalen Druckwechsel, Lunkenbeimer, et al., Anaesthesist 22, 1973, pp. 232–238. Translation Attached (Intrapulmonary Gas Exchange Under Simulated Apnea by Transtracheal, Periodic Intrathoracic Pressure Changes).

Ngeow, et al., A New System for Ventilating with High–Frequency Oscillation. American Physiological Society, 1982, pp. 1638–1642.

\* cited by examiner

*Primary Examiner*—Glenn K. Dawson
(74) *Attorney, Agent, or Firm*—Hodgson Russ LLP

(57) ABSTRACT

A device and method of ventilating a patient reduces the bias flow relative to existing oscillatory ventilators. The device has an oscillator, and an oscillating line having a first end in sealing relationship with the oscillator. A gas supply line is connected to the oscillating line, and a patient line is connected to a second end of the oscillating line. An outlet valve is in pneumatic communication with the patient line. A method of ventilating using such a device is also disclosed.

41 Claims, 8 Drawing Sheets

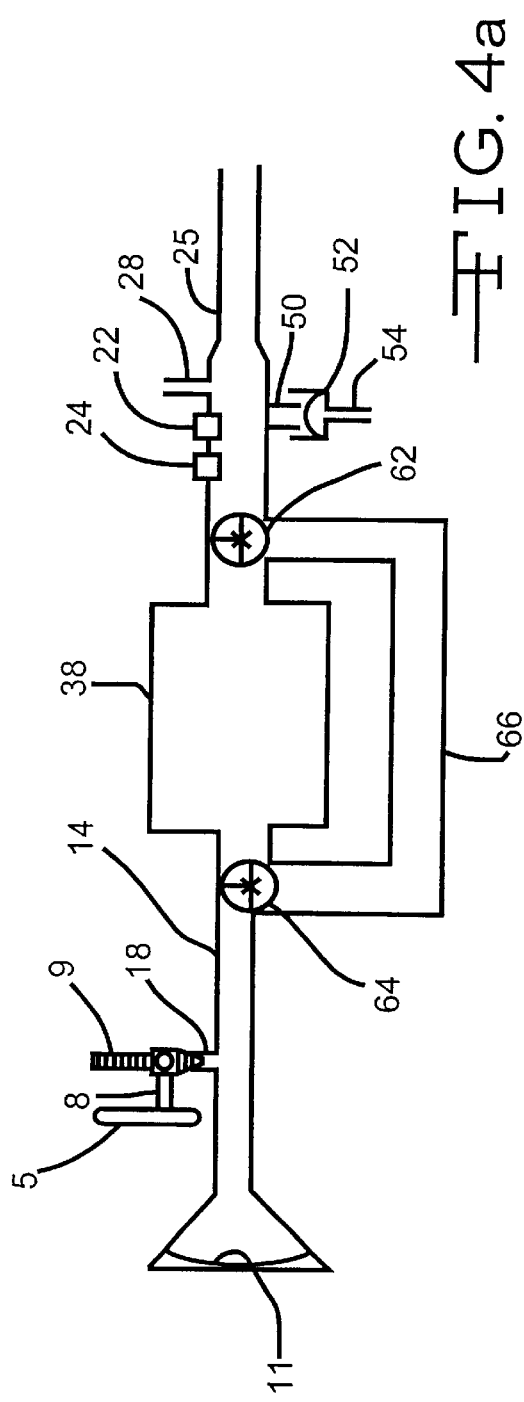
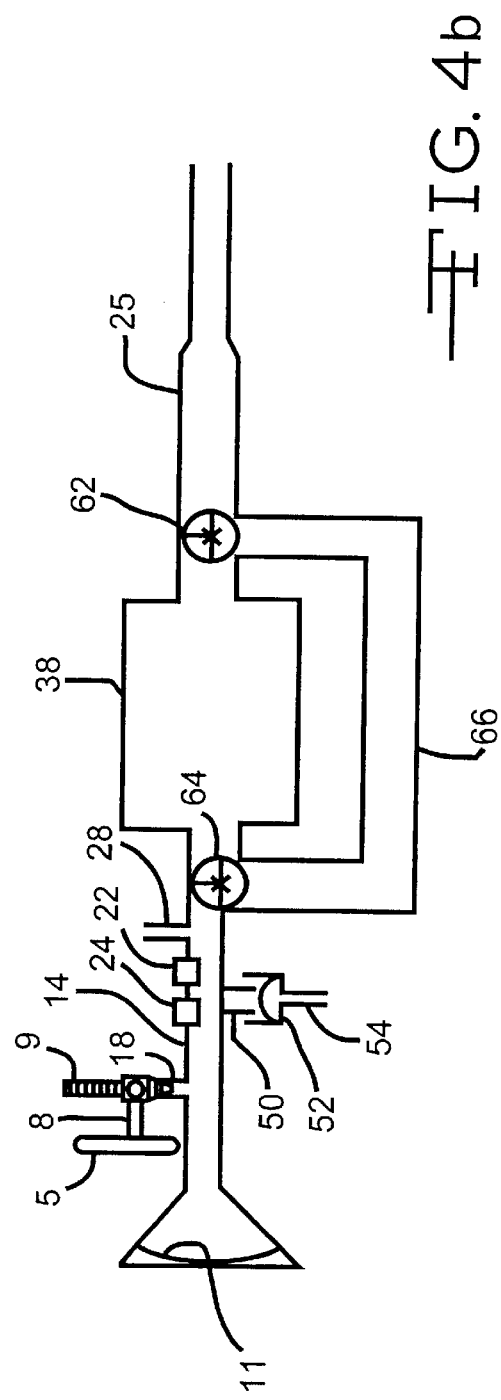

DEVICE AND METHOD OF REDUCING BIAS FLOW IN OSCILLATORY VENTILATORS

CROSS-REFERENCE TO RELATED APPLICATION

This application claims priority to an earlier filed U.S. provisional patent application having serial No. 60/146,863, which was failed on Aug. 3, 1999.

FIELD OF INVENTION

The present invention relates generally to ventilators for supporting breathing in animals. More particularly, the present invention provides a device and method of ventilating.

DISCUSSION OF RELATED ART

There are many situations in which normal breathing by an animal patient is impaired and must be assisted by external means. Oscillatory ventilators are used to facilitate breathing in such situations. Among the types of ventilators available are high frequency oscillating ventilators. U.S. Pat. No. 4,719,910 describes a high frequency oscillating ventilator. A flow of gas is conducted from a gas source to a high frequency oscillator. The high frequency oscillator comprises a housing including a magnet and having a diaphragmatically sealed piston mounted therein, an inlet connecting the space within the housing on the first side of the diaphragm to the gas conducting means, and a coil mounted to the first side of the diaphragm. Circuitry is provided which is operable to reverse the polarity of the flow of the current in the coil, thereby causing the diaphragm to move back and forth within the housing. A tube connecting the space on the second side of the diaphragm to the gas source and the patient's airway is provided.

In the prior art, inspiratory gas is moved into and out of the patient via a U-shaped tube and movement of the diaphragm. For purposes of describing the prior art, the U-shaped tube can be described as having a first limb with a distal end, a second limb with a distal end, and a tube between the limbs. Connected to the tube between the limbs is another tube (the "patient line") that delivers gas from the U-shaped tube to the patient and also delivers gas from the patient to the U-shaped tube. The patient line may be connected to the patient via an endotracheal tube. The distal end of the first limb is placed in sealing relation to the diaphragm so that gas inside the U-shaped tube is caused to oscillate as the diaphragm moves back and forth. Gas suitable for inspiration ("inspiratory gas") is supplied at a location on the U-shaped tube between the diaphragm and the patient line.

Inspiratory gas passes through the first limb of the U-shaped tube, and exhaled gas exits to the atmosphere through the second limb of the U-shaped tube and out of the distal end of the second limb. To prevent expired gases from being drawn back into the first limb during the expiratory phase of breathing, more inspiratory gas than needed by the patient is provided in order to move the expired gas into the second limb. The inspiratory gas provided in excess of the needs of the patient is referred to herein as "bias flow".

To move expired gas into the second limb of the U-shaped tube, an inspiratory gas flow rate of approximately 20 liters per minute is used when ventilating infants, and as much as 60 to 80 liters per minute when ventilating older children and adults. Such large volumes of inspiratory gas would quickly exhaust the available supply of most transport and ambulance vehicles. Furthermore, such prior art devices necessitate large and costly volumes of therapeutic gases that might be mingled with the inspiratory gas (e.g., volatile anesthetics, nitric, oxide, vaporized perfluorocarbons, helium/oxygen mixtures etc.). Finally, such prior art devices are inefficient when one considers the amount of inspiratory gas required by the patient and the relatively large amount of inspiratory gas supplied to the ventilator.

SUMMARY OF THE INVENTION

An object of the present invention is to provide a device and a method of ventilating. The object is achieved by a ventilating device having an oscillator, such as an oscillatory diaphragm, and an oscillating line having a first end in sealing relationship with the oscillator. A gas supply line is connected to the oscillating line, and a patient line is connected to a second end of the oscillating line. An outlet line is in pneumatic communication with the patient line, and an end of the outlet line distal from the patient line is connected to an outlet valve. The outlet valve releases gas from the outlet line during inhalation, and prevents the release of gas from the outlet line during exhalation.

In a method according to the present invention, a ventilation device, such as the one described above, is provided. A patient in pneumatic communication with the patient line is provided and gas is supplied to the oscillating line. The oscillator is moved toward the oscillating line and the outlet valve is opened. Then, the oscillator is moved away from the oscillating line and the outlet valve is closed.

BRIEF DESCRIPTION OF THE DRAWINGS

For a fuller understanding of the nature and objects of the invention, reference should be made to the following description taken in conjunction with the accompanying drawings, in which:

FIGS. 4a and 4b are schematic sectional views of other embodiments of the present invention having a $CO_2$ scrubber;

DETAILED DESCRIPTION OF THE INVENTION

As used herein the term "gas" means a pure gas or a mixture of gases. Thus, the term "gas" may refer to a mixture of $O_2$ and $N_2$, and may include therapeutic gases.

Figure 1:
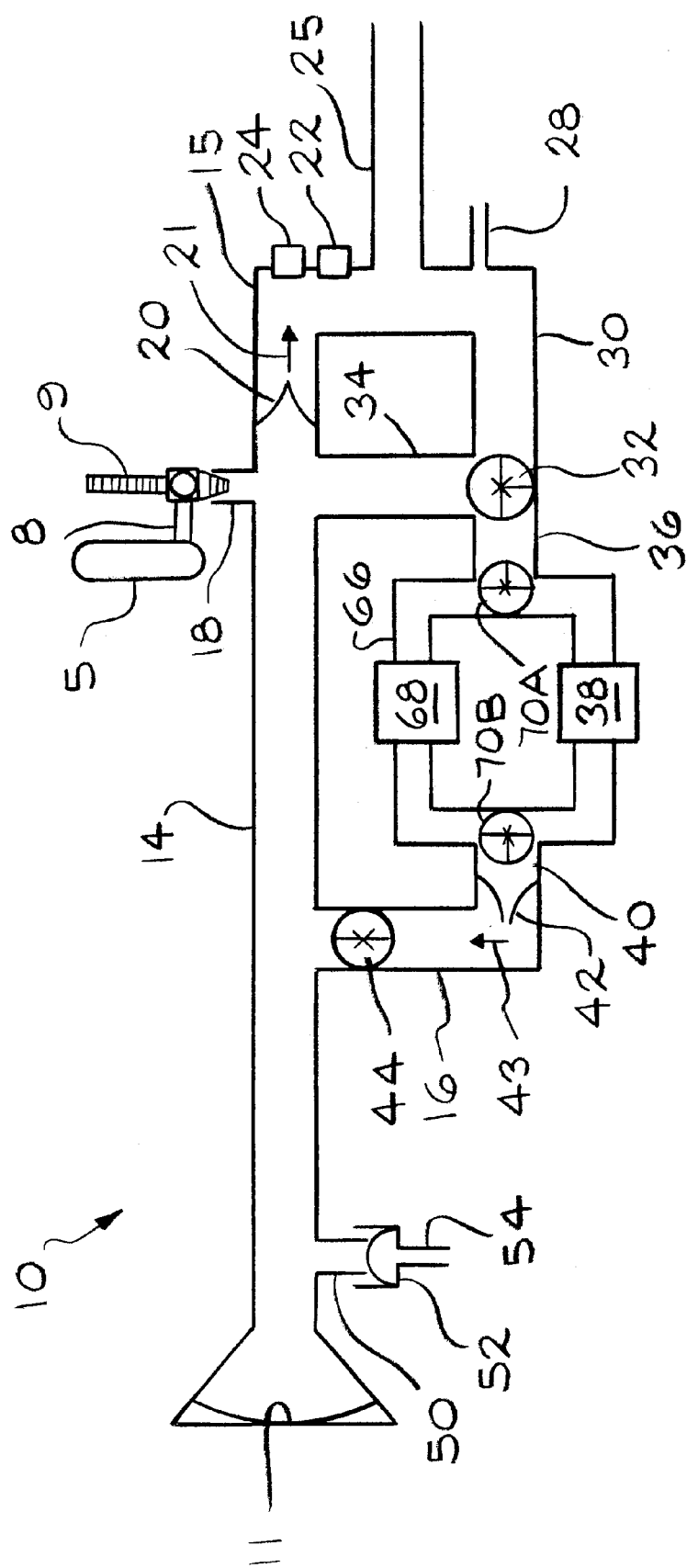
FIG. 1 is a schematic sectional view of a device according to the present invention illustrating the major components of the device and utilizing a $CO_2$ scrubber.

A device 10 according to the present invention can be connected to an oscillating machine having an oscillator 11, such as a diaphragm, like those described in U.S. Pat. No. 4,719,910 and U.S. Pat. No. 5,307,794. As illustrated in FIG. 1, an inspiratory gas source 5 is connected to a device 10 according to the present invention through supply line 8. The flow of inspiratory gas into the device 10 can be regulated by a flow regulator 9 connected to supply line 8. Preferably, the flow of inspiratory gas from supply line 8 and into connecting line 18 is essentially at a constant rate. Connecting line 18 is connected to the oscillating line 14.

In the embodiment shown in FIG. 1, an inbound check valve 20 is in the oscillating line 14. The portion of the oscillating line 14 that is downstream of the inbound check valve 20 is referred to herein as the inbound line 15. The check valve 20 permits the flow of gas in the direction of arrow 21 and prevents the flow of gas in the opposite direction. When the pressure on the upstream side of the inbound check valve 20 is higher than the pressure on the downstream side of the inbound check valve 20, the inbound check valve 20 opens allowing gas to flow in the direction of arrow 21. When the pressure on the upstream side of the inbound check valve 20 is lower than on the downstream side, the inbound check valve 20 shuts, effectively stopping the flow of gas through inbound line 15.

Further downstream of inbound check valve 20, for example along inbound line 15 may be placed an $O_2$ sensor 24 and a $CO_2$ sensor 22 to monitor the quality of the gas therein. Additional modifiers and monitors like humidifiers, nebulizers and the like can also be installed. Inbound line 15 connects to patient line 25, which is in turn connected to an endotracheal tube (not shown in FIG. 1) for delivery of gas to the patient's airways, and ultimately to the patient's lungs.

Inbound line 15 is also connected to exhalation line 30. In exhalation line 30 may be placed a pressure monitoring device, such as a manometer, through port 28. Exhalation line 30 includes a scrubber line 36 and connects to recirculation line 34. Recirculation line 34 connects to the oscillating line 14. At the junction of recirculation line 34 and scrubber line 36 is a two-position valve 32 which directs the flow of gas either toward the recirculation line 34 or toward the scrubber line 36. The two position valve 32 is normally positioned to direct the flow of gas to the scrubber line 36. Preferably, the two-position valve 32 is normally adjusted so that no gas flows through recirculation line 34.

Included in the exhalation line 30 is a scrubber canister 38, an outbound line 40, and a discharge line 16. A second scrubber 68 may also be included and used when the scrubber canister 38 is not being used, for example, while scrubber canister 38 is being replaced or recharged, for example, by purging $CO_2$ using a separate flow of gas (not shown). The scrubber valves 70A and 70B preferably operate together so that either scrubber canister 38 or the second scrubber 68 is in operation. In a preferred embodiment, the scrubber valves 70A and 70B are not two separate valves, but instead a slide type valve, commonly used in the medical community, having an outer cylindrical shell and a movable inner cylinder, each with holes therethrough that allow either the scrubber canister 38 or the second scrubber 68 to be in service.

The outbound line 40 is fitted with an outbound check valve 42, which permits the flow of gas in the direction of arrow 43 and prevents the flow of gas in the opposite direction. Downstream of the outbound check valve 42 is discharge line 16 having within it a shut-off valve 44. The shut-off valve 44 is normally set to the open position. The shut-off valve 44 in its open position, permits the flow of gas, but in its closed position blocks the flow of gas. Discharge line 16 connects to oscillating line 14.

Figure 2A:
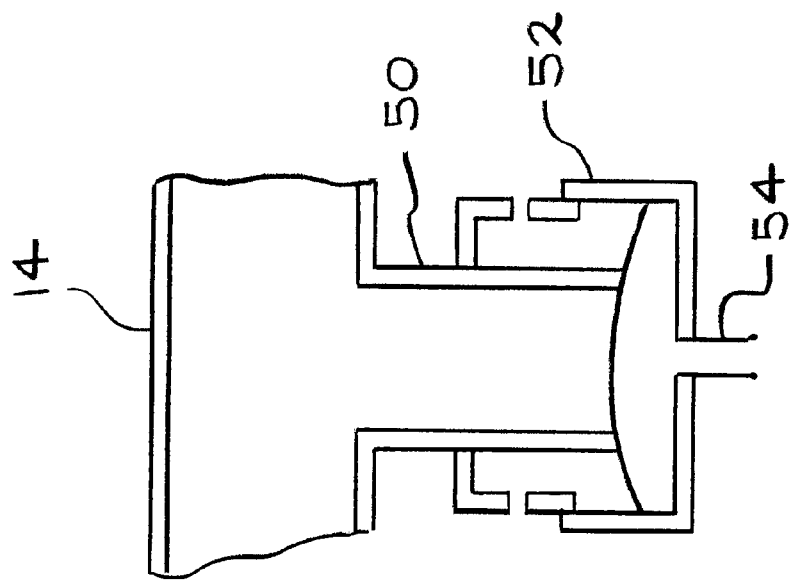
FIGS. 2a and 2b are schematic sectional representations of the closed and open positions respectively of an outlet valve according to the present invention.
Figure 2B:
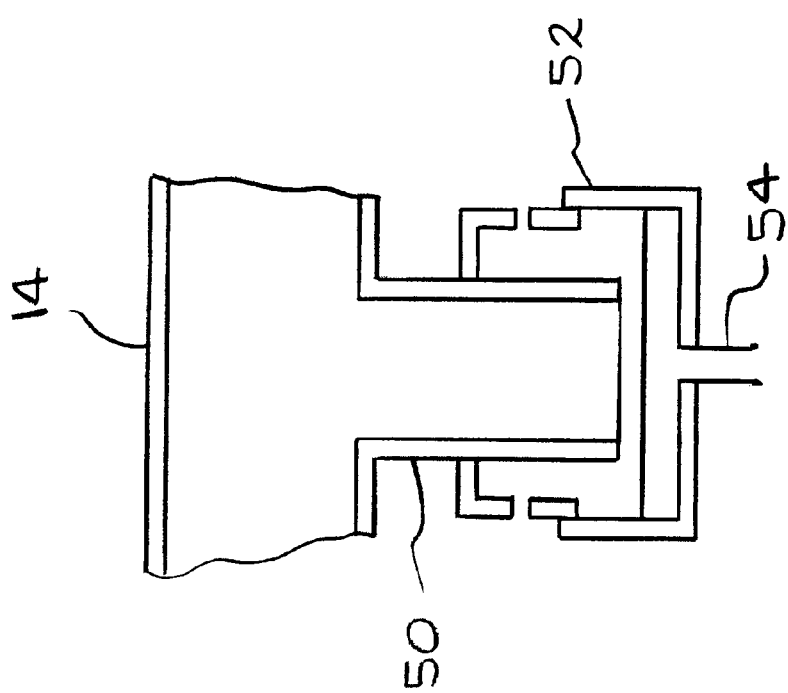

Oscillating line 14 connects at one end to the patient line 25, and is placed in sealing relationship at the other end with the oscillator 11. Preferably, the oscillator 11 is a diaphragm of a high frequency oscillating machine. Connected to the oscillating line 14 is an outlet line 50, which is in turn connected to outlet valve 52. The outlet valve 52 may open and shut in response to a control pressure provided via control line 54. The closed and open positions of outlet valve 52 are shown in FIGS. 2a and 2b respectively. The external control pressure may be provided to control line 54 by the oscillating machine that controls the oscillator 11. In one embodiment of the present invention, the control pressure provided by line 54 is substantially stable and the oscillating pressure in line 14 caused by movement of the diaphragm 11 causes the outlet valve 52 to open and close. Alternatively, operation of the outlet valve 52 may be by other means, such as a solenoid.

High frequency oscillation of the oscillator 11 facilitates movement of gas into and out of the patient's airways. Thus, during the inspiration phase, when the oscillator 11 is moving toward the oscillating line 14, a pressurizing cycle occurs, and during the expiration phase, when the oscillator 11 is moving away from the oscillating line 14, a depressurizing cycle occurs. During the pressurizing cycle, the pressure on the upstream side of the inbound check valve 20 increases, forcing it to open thereby allowing gas to flow in the direction of arrow 21, and consequently into the patient's lungs via patient line 25. At the same time, due to the oscillator 11 moving toward the device 10, the pressure on the downstream side of outbound check valve 42 becomes higher than the pressure on its upstream side, which forces the outbound check valve 42 to close, thereby preventing the flow of gas from discharge line 16 into the scrubber canister 38.

During the expiration phase (or depressurizing part of the cycle), the oscillator 11 moves away from the oscillating line 14 and the pressure differential across the inbound check valve 20 causes the inbound check valve 20 to close. The exhaled gas is pushed by the patient's lungs into exhalation line 30, and into the $CO_2$ scrubber canister 38. At the same time, the pressure differential across the outbound check valve 42 causes the outbound check valve 42 to open. Thus, $CO_2$ scrubbed gas is returned to oscillating line 14 through the normally open shut-off valve 44. The gas returning to the oscillating line 14 via the discharge line 16 mixes with the gas in the oscillating line 14. The gas in oscillating line 14 is moved toward the outlet valve 52 when the inbound check valve 20 is closed by the movement of the oscillator 11. FIGS. 2a and 2b illustrate the open and closed positions of the pneumatic version of the outlet valve 52. When the control pressure supplied by control line 54 exceeds the pressure in the oscillating line 14 (FIG. 2a), the outlet valve 52 is in the closed position and gas from oscillating line 14 is prevented from escaping from the device 10. When the control pressure supplied by control line 54 is less than the pressure in the oscillating line 14 (FIG. 2b), the outlet valve 52 is in the open position and gas from oscillating line 14 is allowed to escape from the device 10. In the embodiments shown in FIGS. 1 through 5, preferably the outlet valve 52 is closed for at least part of the expiration phase (i.e. when the pressure in oscillating line 14 is decreasing due to movement of the oscillator 11 away from the device 10), and the outlet valve 52 is open for at least part of the inspiration phase (i.e. when the pressure in oscillating line 14 is increasing due to movement of the oscillator 11 toward the device 10).

Figure 3A:
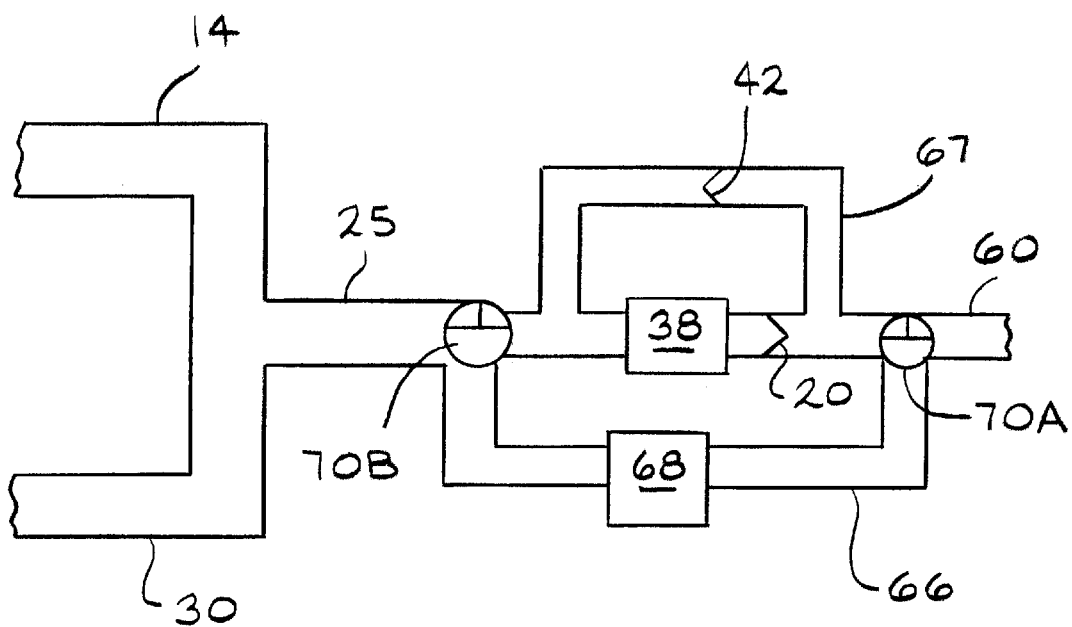
FIG. 3a is a schematic sectional representation of another embodiment of the present invention.
Figure 3B:
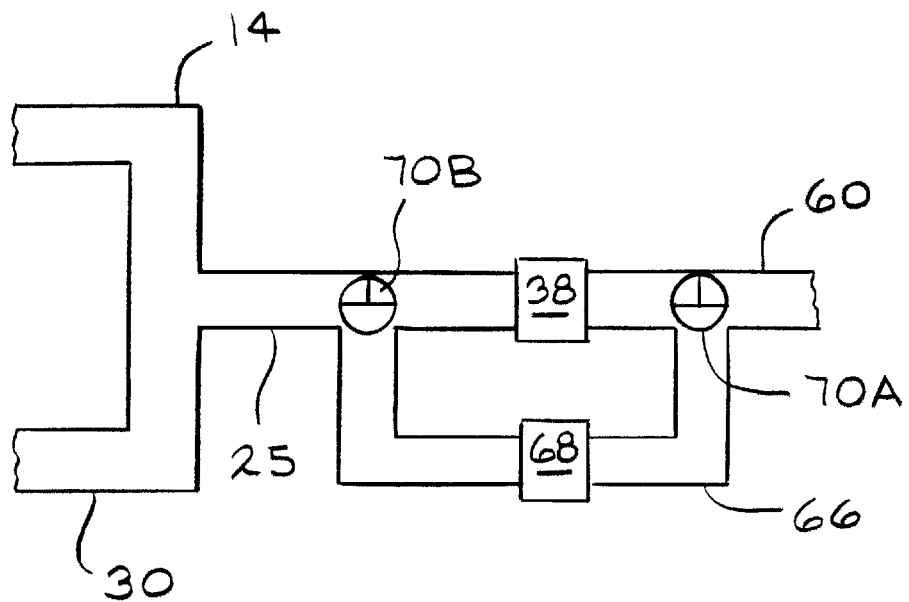
FIG. 3b is a schematic sectional representation of another embodiment of the present invention.

The $CO_2$ scrubber canister 38 in the device 10 of the present invention may be used in other locations. For example, as shown in FIGS. 3a and 3b, the scrubber canister 38 may be placed at the end of patient line 25 distal from the inbound line 15, and preferably between the patient line 25 and the endotracheal tube 60. As shown in FIG. 3a, suitable check valves 20, 42 and return line 67 can be incorporated to assure unidirectional flow through the scrubber canister 38. As shown in FIGS. 3a and 3b, a bypass line 66 could be provided to accommodate replacement of the scrubber canister 38. In a preferred embodiment of the present invention, the second scrubber canister 68 is provided in the bypass line 66. The second scrubber canister 68 may be incorporated into any embodiment described herein which has a scrubber canister 38. The device depicted in FIGS. 3a and 3b could be used with prior art ventilator circuits.

The scrubber canister 38 contains a material that removes unwanted gas, such as $CO_2$. For example, the scrubber canister 38 may contain sodium hydroxide, calcium hydroxide, or barium hydroxide. Sodium hydroxide and calcium hydroxide mixed with silica is available as Soda Lime™. Another commercially available $CO_2$ scrubber is Baralyme™ which comprises barium hydroxide and calcium hydroxide. Once the $CO_2$ scrubber canister 38 is depleted of its scrubbing capacity, it can be replaced. To replace the scrubber canister 38, the two-position valve 32 is set to direct the gas from the exhalation line 30 to the recirculation line 34, while the shut-off valve 44 is set to the closed position. Upon replacement of the scrubber canister 38, the two-position valve 32 and the shut-off valve 44 are reset to their normal positions.

FIGS. 4a and 4b show two additional embodiments of the present invention. As illustrated in FIG. 4a, the scrubber canister 38 may be placed in the oscillating line 14 upstream of the $CO_2$ and $O_2$ sensors 22, 24, or as shown in FIG. 4b, downstream of the sensors 22, 24. In the embodiments shown in FIGS. 4a and 4b, check valves are not required to direct the flow of inspiratory gas toward the patient line 25 or to direct the flow of expired gas toward the scrubber canister 38. Normally, gas moves in both directions through the scrubber canister 38. To replace the scrubber canister 38, two block valves 62,64 can be temporarily adjusted so that gas flows through the bypass line 66.

Figure 5:
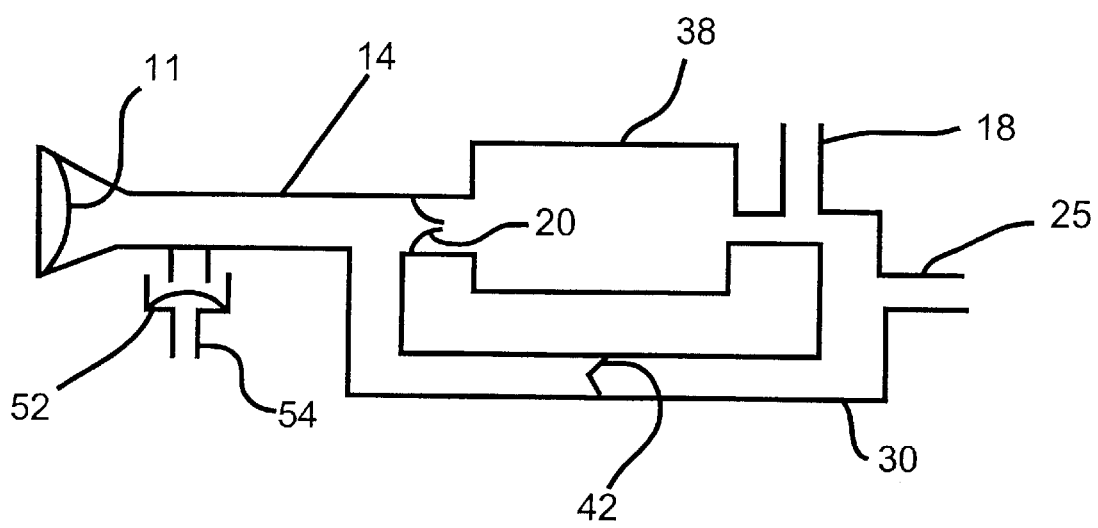
FIG. 5 is a schematic sectional representation of another embodiment of the present invention.

FIG. 5 shows another embodiment of the present invention in which the scrubber is located in the oscillating line 14, and gas flows through the scrubber canister 38 toward the patient line 25. Flow from the patient line 25 moves through the exhalation line 30 to oscillating line 14. A check valve 42 is in bypass line 66 to assure that flow moves through exhalation line 30 in one direction only. An additional check valve 20 may be included in oscillating line 14 to assure flow through the scrubber canister 38 in one direction only.

Figure 6:
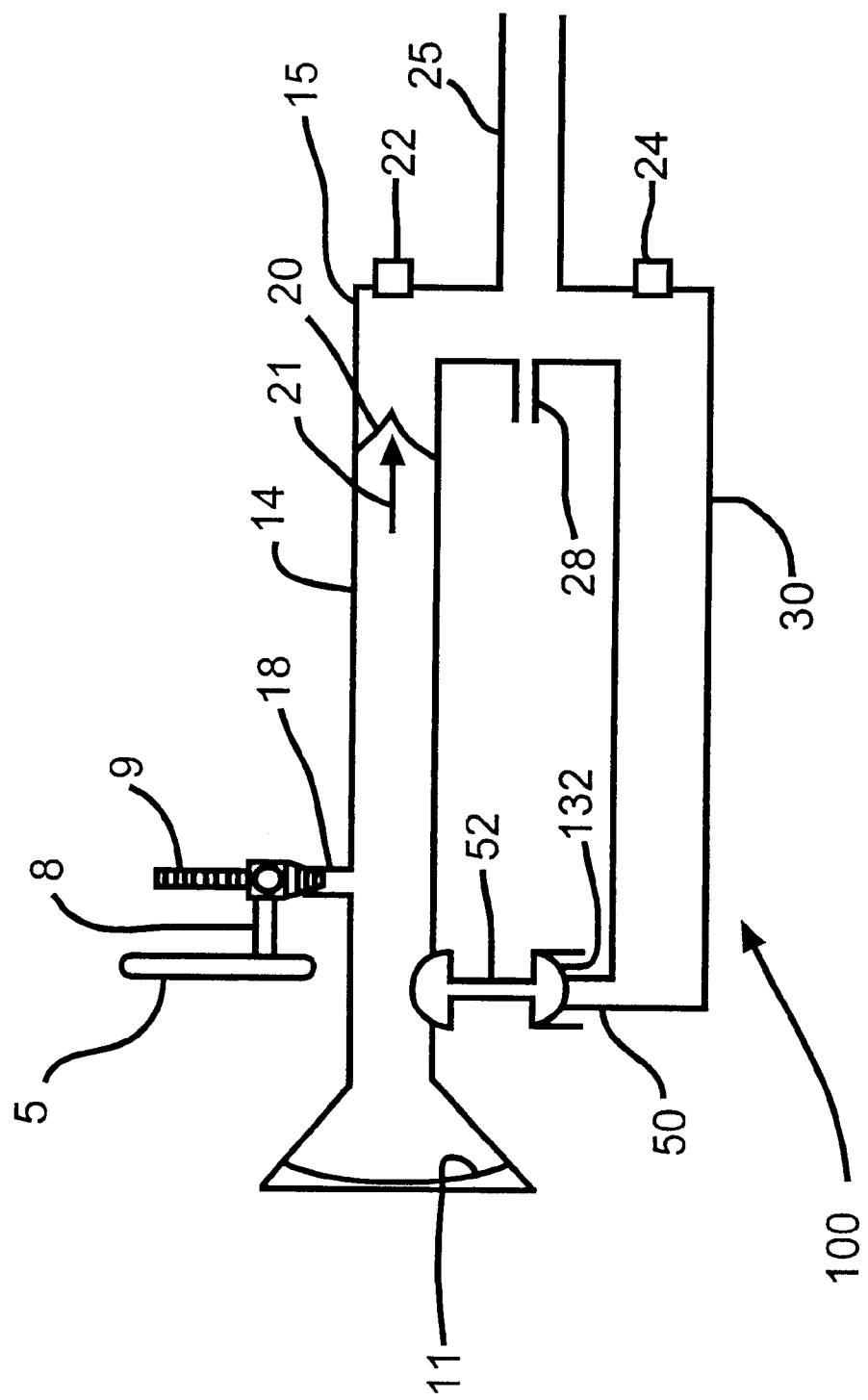
FIG. 6 is a schematic sectional view of another embodiment of the invention without a $CO_2$ scrubber.

In another embodiment of the present invention, illustrated in FIG. 6, instead of scrubbing $CO_2$ from the exhaled gas, the exhaled gas is simply allowed to leave a device 100. The device 100 is connected to an inspiratory gas source 5 through connecting line 18. The inspiratory gas enters an oscillating line 14 and moves toward the patient line 25 in the direction of arrow 21 via the inbound check valve 20. $CO_2$ and $O_2$ sensors 22, 24 and pressure monitoring port 28 can be placed near the patient line 25. The exhaled gas is conducted by the exhalation line 30 to another type of outlet valve 52. The outlet valve 52 shown in FIGS. 6, 7a and 7b operates based on the pressure differential between oscillating line 14 and the exhalation line 30. During the pressurizing cycle, outlet valve 52 is caused to close the end 132 of exhalation line 30 by the rising pressure in oscillating line 14. However, during the depressurizing phase, the pressure in the outlet line 50 causes the outlet valve 52 to open the end 132 and allow gas to escape to the atmosphere. Preferably, for at least part of the pressurization cycle, outlet valve 52 is closed and there is no communication between the exhalation line 30 and the atmosphere, and for at least part of the depressurization cycle, outlet valve 52 is open and there is communication between line 30 and the atmosphere.

Figure 7A:
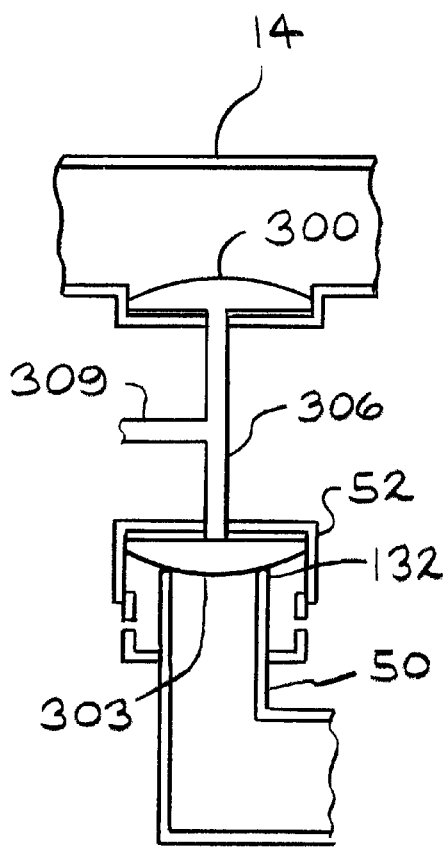
FIGS. 7a and 7b are schematic sectional representations of the closed and open positions respectively of another outlet valve according to the present invention.
Figure 7B:
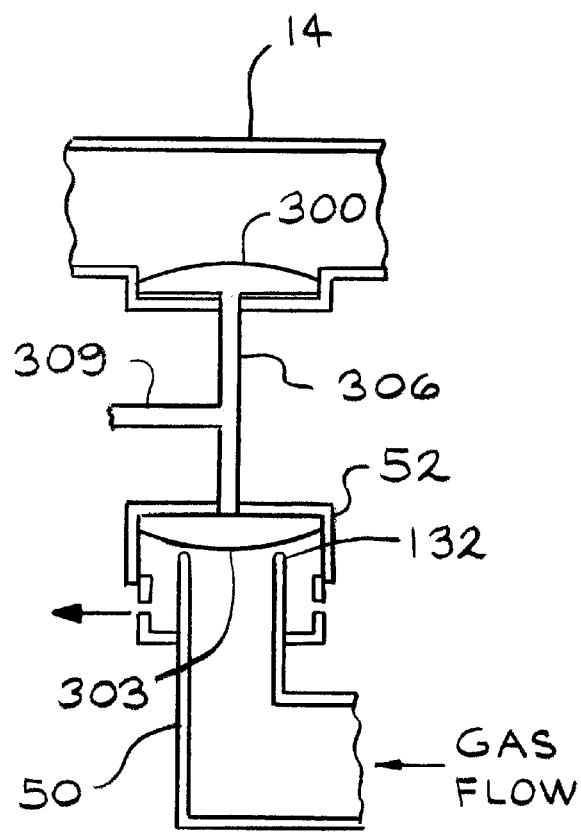

FIGS. 7a and 7b show a preferred embodiment of the outlet valve 52 shown in FIG. 6. The outlet valve 52 in FIGS. 7a and 7b has a first flexible membrane 300 disposed in the oscillating line 14 and a second flexible membrane 303 situated to selectively close the end 132 of the outlet line 50. The flexible membranes 300, 303 are connected by a pressure communication line 306. The pressure communication line 306 may be filled with a gas or a fluid. When the pressure in the pressure communication line 306 is above the pressure in outlet line 50, the end 132 of the outlet line 50 is closed by the second flexible membrane 303. When the pressure in the outlet line 50 is above the pressure in the pressure communication line 306, gas is allowed to escape from the end 132 of the outlet line 50. It will be recognized that due to the first flexible membrane 300, the pressure in oscillating line 14 will change the pressure in the pressure communication line 306.

In a preferred embodiment, a control pressure line 309 is connected to the pressure communication line 306. When the control pressure line 309 is provided, the pressure in the pressure communication line 306 may be changed, and thereby, the pressure in the outlet line 50 required to open the end 132 of the outlet line 50 may be changed.

To illustrate the concept of the present invention, mathematical relationships were developed for the device 10 shown in FIG. 1. Tables 1–10 below list data corresponding to these mathematical relationships. In the tables:

$VO_2$ is the volume rate of oxygen consumed by the patient;

VI is the volume rate of inspiratory gas supplied to the device 10;

$FiO_2$ is the mole fraction of oxygen in the inspiratory gas;

$FmO_2$ is the mole fraction of oxygen in the mixed gas crossing inbound check valve 20;

$FiO_2 = 1-FiN_2$, where $FiN_2$ is the mole fraction of nitrogen in the inspiratory gas;

$FmO_2 = 1-FmN_2$, where $FmN_2$ is the mole fraction of nitrogen in the mixed gas exiting the outlet valve 52;

$VI = K+VO_2$, where K=outflow volume from outlet valve 52;

$VI \times FiN_2 = K \times FmN_2$;

$VI(1-FiO_2) = K(1-FmO_2)$;

$(VI \div K)(1-FiO_2) = 1-FmO_2$;

$FmO_2 = 1-((VI \div K)(1-FiO_2))$.

TABLE 1

| $VO_2$ ml/kg/ min | VI ml/kg/ min | $FiO_2$ | $FmO_2$ | $FmO_2 \div FiO_2$ | K ml/kg/ min | $VI \div VO_2$ |
|---|---|---|---|---|---|---|
| 5.0 | 6.0 | 0.21 | −3.74 | −17.81 | 1.0 | 1.2 |
| 5.0 | 10.0 | 0.21 | −0.58 | −2.76 | 5.0 | 2.0 |
| 5.0 | 20.0 | 0.21 | −0.05 | −0.25 | 15.0 | 4.0 |
| 5.0 | 30.0 | 0.21 | 0.05 | 0.25 | 25.0 | 6.0 |
| 5.0 | 40.0 | 0.21 | 0.10 | 0.46 | 35.0 | 8.0 |

TABLE 1-continued

| $VO_2$ ml/kg/min | VI ml/kg/min | $FiO_2$ | $FmO_2$ | $FmO_2 \div FiO_2$ | K ml/kg/min | $VI \div VO_2$ |
|---|---|---|---|---|---|---|
| 5.0 | 50.0 | 0.21 | 0.12 | 0.58 | 45.0 | 10.0 |
| 5.0 | 60.0 | 0.21 | 0.14 | 0.66 | 55.0 | 12.0 |
| 5.0 | 70.0 | 0.21 | 0.15 | 0.71 | 65.0 | 14.0 |
| 5.0 | 80.0 | 0.21 | 0.16 | 0.75 | 75.0 | 16.0 |
| 5.0 | 90.0 | 0.21 | 0.16 | 0.78 | 85.0 | 18.0 |
| s.0 | 100.0 | 0.21 | 0.17 | 0.80 | 95.0 | 20.0 |
| 5.0 | 200.0 | 0.21 | 0.19 | 0.90 | 195.0 | 40.0* |
| 5.0 | 500.0 | 0.21 | 0.20 | 0.96 | 495.0 | 100.0 |
| 5.0 | 1000.0 | 0.21 | 0.21 | 0.98 | 995.0 | 200.0 |

TABLE 2

| $VO_2$ ml/kg/min | VI ml/kg/min | $FiO_2$ | $FmO_2$ | $FmO_2 \div FiO_2$ | K ml/kg/min | $VI \div VO_2$ |
|---|---|---|---|---|---|---|
| 5.0 | 6.0 | 0.30 | −3.20 | −10.67 | 1.0 | 1.2 |
| 5.0 | 10.0 | 0.30 | −0.40 | −1.33 | 5.0 | 2.0 |
| 5.0 | 20.0 | 0.30 | 0.07 | 0.22 | 15.0 | 4.0 |
| 5.0 | 30.0 | 0.30 | 0.16 | 0.53 | 25.0 | 6.0 |
| 5.0 | 40.0 | 0.30 | 0.20 | 0.67 | 35.0 | 8.0 |
| 5.0 | 50.0 | 0.30 | 0.22 | 0.74 | 45.0 | 10.0 |
| 5.0 | 60.0 | 0.30 | 0.24 | 0.79 | 55.0 | 12.0 |
| 5.0 | 70.0 | 0.30 | 0.25 | 0.82 | 65.0 | 14.0 |
| 5.0 | 80.0 | 0.30 | 0.25 | 0.84 | 75.0 | 16.0 |
| 5.0 | 90.0 | 0.30 | 0.26 | 0.86 | 85.0 | 18.0 |
| 5.0 | 100.0 | 0.30 | 0.26 | 0.88 | 95.0 | 20.0 |
| 5.0 | 200.0 | 0.30 | 0.28 | 0.94 | 195.0 | 40.0* |
| 5.0 | 500.0 | 0.30 | 0.29 | 0.98 | 495.0 | 100.0 |
| 5.0 | 1000.0 | 0.30 | 0.30 | 0.99 | 995.0 | 200.0 |

TABLE 3

| $VO_2$ ml/kg/min | VI ml/kg/min | $FiO_2$ | $FmO_2$ | $FmO_2 \div FiO_2$ | K ml/kg/min | $VI \div VO_2$ |
|---|---|---|---|---|---|---|
| 5.0 | 6.0 | 0.40 | −2.60 | −6.50 | 1.0 | 1.2 |
| 5.0 | 10.0 | 0.40 | −0.20 | −0.5O | 5.0 | 2.0 |
| 5.0 | 20.0 | 0.40 | 0.20 | 0.50 | 15.0 | 4.0 |
| 5.0 | 30.0 | 0.40 | 0.28 | 0.70 | 25.0 | 6.0 |
| 5.0 | 40.0 | 0.40 | 0.31 | 0.79 | 35.0 | 8.0 |
| 5.0 | 50.0 | 0.40 | 0.33 | 0.83 | 45.0 | 10.0 |
| 5.0 | 60.0 | 0.40 | 0.35 | 0.86 | 55.0 | 12.0 |
| 5.0 | 70.0 | 0.40 | 0.35 | 0.88 | 65.0 | 14.0 |
| 5.0 | 80.0 | 0.40 | 0.36 | 0.90 | 75.0 | 16.0* |
| 5.0 | 90.0 | 0.40 | 0.36 | 0.91 | 85.0 | 18.0 |
| 5.0 | 100.0 | 0.40 | 0.37 | 0.92 | 95.0 | 20.0 |
| 5.0 | 200.0 | 0.40 | 0.38 | 0.96 | 195.0 | 40.0 |
| 5.0 | 500.0 | 0.40 | 0.39 | 0.98 | 495.0 | 100.0 |
| 5.0 | 1000.0 | 0.40 | 0.40 | 0.99 | 995.0 | 200.0 |

TABLE 4

| $VO_2$ ml/kg/min | VI ml/kg/min | $FiO_2$ | $FmO_2$ | $FmO_2 \div FiO_2$ | K ml/kg/min | $VI \div VO_2$ |
|---|---|---|---|---|---|---|
| 5.0 | 6.0 | 0.50 | −2.00 | −4.00 | 1.0 | 1.2 |
| 5.0 | 10.0 | 0.50 | 0.00 | 0.00 | 5.0 | 2.0 |
| 5.0 | 20.0 | 0.50 | 0.33 | 0.67 | 15.0 | 4.0 |
| 5.0 | 30.0 | 0.50 | 0.40 | 0.80 | 25.0 | 6.0 |
| 5.0 | 40.0 | 0.50 | 0.43 | 0.86 | 35.0 | 8.0 |
| 5.0 | 50.0 | 0.50 | 0.44 | 0.89 | 45.0 | 10.0 |
| 5.0 | 60.0 | 0.50 | 0.45 | 0.91 | 55.0 | 12.0* |
| 5.0 | 70.0 | 0.50 | 0.46 | 0.92 | 65.0 | 14.0 |
| 5.0 | 80.0 | 0.50 | 0.47 | 0.93 | 75.0 | 16.0 |
| 5.0 | 90.0 | 0.50 | 0.47 | 0.94 | 85.0 | 18.0 |

TABLE 4-continued

| $VO_2$ ml/kg/min | VI ml/kg/min | $FiO_2$ | $FmO_2$ | $FmO_2 \div FiO_2$ | K ml/kg/min | $VI \div VO_2$ |
|---|---|---|---|---|---|---|
| 5.0 | 100.0 | 0.50 | 0.47 | 0.95 | 95.0 | 20.0 |
| 5.0 | 200.0 | 0.50 | 0.49 | 0.97 | 195.0 | 40.0 |
| 5.0 | 500.0 | 0.50 | 0.49 | 0.99 | 495.0 | 100.0 |
| 5.0 | 1000.0 | 0.50 | 0.50 | 0.99 | 995.0 | 200.0 |

TABLE 5

| $VO_2$ ml/kg/min | VI ml/kg/min | $FiO_2$ | $FmO_2$ | $FmO_2 \div FiO_2$ | K ml/kg/min | $VI \div VO_2$ |
|---|---|---|---|---|---|---|
| 5.0 | 6.0 | 0.60 | −1.40 | −2.33 | 1.0 | 1.2 |
| 5.0 | 10.0 | 0.60 | 0.20 | 0.33 | 5.0 | 2.0 |
| 5.0 | 20.0 | 0.60 | 0.47 | 0.78 | 15.0 | 4.0 |
| 5.0 | 30.0 | 0.60 | 0.52 | 0.87 | 25.0 | 6.0 |
| 5.0 | 40.0 | 0.60 | 0.54 | 0.90 | 35.0 | 8.0* |
| 5.0 | 50.0 | 0.60 | 0.56 | 0.93 | 45.0 | 10.0 |
| 5.0 | 60.0 | 0.60 | 0.56 | 0.94 | 55.0 | 12.0 |
| 5.0 | 70.0 | 0.60 | 0.57 | 0.95 | 65.0 | 14.0 |
| 5.0 | 80.0 | 0.60 | 0.57 | 0.96 | 75.0 | 16.0 |
| 5.0 | 90.0 | 0.60 | 0.58 | 0.96 | 85.0 | 18.0 |
| 5.0 | 100.0 | 0.60 | 0.58 | 0.96 | 95.0 | 20.0 |
| 5.0 | 200.0 | 0.60 | 0.59 | 0.98 | 195.0 | 40.0 |
| 5.0 | 500.0 | 0.60 | 0.60 | 0.99 | 495.0 | 100.0 |
| 5.0 | 1000.0 | 0.60 | 0.60 | 1.00 | 995.0 | 200.0 |

TABLE 6

| $VO_2$ ml/kg/min | VI ml/kg/min | $FiO_2$ | $FmO_2$ | $FmO_2 \div FiO_2$ | K ml/kg/min | $VI \div VO_2$ |
|---|---|---|---|---|---|---|
| 5.0 | 6.0 | 0.70 | −0.80 | −1.14 | 1.0 | 1.2 |
| 5.0 | 10.0 | 0.70 | 0.40 | 0.57 | 5.0 | 2.0 |
| 5.0 | 20.0 | 0.70 | 0.60 | 0.86 | 15.0 | 4.0 |
| 5.0 | 30.0 | 0.70 | 0.64 | 0.91 | 25.0 | 6.0* |
| 5.0 | 40.0 | 0.70 | 0.67 | 0.94 | 35.0 | 8.0 |
| 5.0 | 50.0 | 0.70 | 0.67 | 0.95 | 45.0 | 10.0 |
| 5.0 | 60.0 | 0.70 | 0.68 | 0.96 | 55.0 | 12.0 |
| 5.0 | 70.0 | 0.70 | 0.68 | 0.97 | 65.0 | 14.0 |
| 5.0 | 80.0 | 0.70 | 0.68 | 0.97 | 75.0 | 16.0 |
| 5.0 | 90.0 | 0.70 | 0.68 | 0.97 | 85.0 | 18.0 |
| 5.0 | 100.0 | 0.70 | 0.68 | 0.98 | 95.0 | 20.0 |
| 5.0 | 200.0 | 0.70 | 0.69 | 0.99 | 195.0 | 40.0 |
| 5.0 | 500.0 | 0.70 | 0.70 | 1.00 | 495.0 | 100.0 |
| 5.0 | 1000.0 | 0.70 | 0.70 | 1.00 | 995.0 | 200.0 |

TABLE 7

| $VO_2$ ml/kg/min | VI ml/kg/min | $FiO_2$ | $FmO_2$ | $FmO_2 \div FiO_2$ | K ml/kg/min | $VI \div VO_2$ |
|---|---|---|---|---|---|---|
| 5.0 | 6.0 | 0.80 | −0.20 | −0.25 | 1.0 | 1.2 |
| 5.0 | 10.0 | 0.80 | 0.60 | 0.75 | 5.0 | 2.0 |
| 5.0 | 20.0 | 0.80 | 0.73 | 0.92 | 15.0 | 4.0* |
| 5.0 | 30.0 | 0.80 | 0.76 | 0.95 | 25.0 | 6.0 |
| 5.0 | 40.0 | 0.80 | 0.77 | 0.96 | 35.0 | 8.0 |
| 5.0 | 50.0 | 0.80 | 0.78 | 0.97 | 45.0 | 10.0 |
| 5.0 | 60.0 | 0.80 | 0.78 | 0.98 | 55.0 | 12.0 |
| 5.0 | 70.0 | 0.80 | 0.78 | 0.98 | 65.0 | 14.0 |
| 5.0 | 80.0 | 0.80 | 0.79 | 0.98 | 75.0 | 16.0 |
| 5.0 | 90.0 | 0.80 | 0.79 | 0.99 | 85.0 | 18.0 |
| 5.0 | 100.0 | 0.80 | 0.79 | 0.99 | 95.0 | 20.0 |
| 5.0 | 200.0 | 0.80 | 0.79 | 0.99 | 195.0 | 40.0 |
| 5.0 | 500.0 | 0.80 | 0.80 | 1.00 | 495.0 | 100.0 |
| 5.0 | 1000.0 | 0.80 | 0.80 | 1.00 | 995.0 | 200.0 |

TABLE 8

| $VO_2$ ml/kg/min | VI ml/kg/min | $FiO_2$ | $FmO_2$ | $FmO_2 \div FiO_2$ | K ml/kg/min | $VI \div VO_2$ |
|---|---|---|---|---|---|---|
| 5.0 | 6.0 | 0.90 | 0.40 | 0.44 | 1.0 | 1.2 |
| 5.0 | 10.0 | 0.90 | 0.80 | 0.89 | 5.0 | 2.0 |
| 5.0 | 20.0 | 0.90 | 0.87 | 0.96 | 15.0 | 4.0* |
| 5.0 | 30.0 | 0.90 | 0.88 | 0.98 | 25.0 | 6.0 |
| 5.0 | 40.0 | 0.90 | 0.89 | 0.98 | 35.0 | 8.0 |
| 5.0 | 50.0 | 0.90 | 0.89 | 0.99 | 45.0 | 10.0 |
| 5.0 | 60.0 | 0.90 | 0.89 | 0.99 | 55.0 | 12.0 |
| 5.0 | 70.0 | 0.90 | 0.89 | 0.99 | 65.0 | 14.0 |
| 5.0 | 80.0 | 0.90 | 0.89 | 0.99 | 75.0 | 16.0 |
| 5.0 | 90.0 | 0.90 | 0.89 | 0.99 | 85.0 | 18.0 |
| 5.0 | 100.0 | 0.90 | 0.89 | 0.99 | 95.0 | 20.0 |
| 5.0 | 200.0 | 0.90 | 0.90 | 1.00 | 195.0 | 40.0 |
| 5.0 | 500.0 | 0.90 | 0.90 | 1.00 | 495.0 | 100.0 |
| 5.0 | 1000.0 | 0.90 | 0.90 | 1.00 | 995.0 | 200.0 |

TABLE 9

| $VO_2$ ml/kg/min | VI ml/kg/min | $FiO_2$ | $FmO_2$ | $FmO_2 \div FiO_2$ | K ml/kg/min | $VI \div VO_2$ |
|---|---|---|---|---|---|---|
| 5.0 | 6.0 | 1.00 | 1.00 | 1.00 | 1.0 | 1.2* |
| 5.0 | 10.0 | 1.00 | 1.00 | 1.00 | 5.0 | 2.0 |
| 5.0 | 20.0 | 1.00 | 1.00 | 1.00 | 15.0 | 4.0 |
| 5.0 | 30.0 | 1.00 | 1.00 | 1.00 | 25.0 | 6.0 |
| 5.0 | 40.0 | 1.00 | 1.00 | 1.00 | 35.0 | 8.0 |
| 5.0 | 50.0 | 1.00 | 1.00 | 1.00 | 45.0 | 10.0 |
| 5.0 | 60.0 | 1.00 | 1.00 | 1.00 | 55.0 | 12.0 |
| 5.0 | 70.0 | 1.00 | 1.00 | 1.00 | 65.0 | 14.0 |
| 5.0 | 80.0 | 1.00 | 1.00 | 1.00 | 75.0 | 16.0 |
| 5.0 | 90.0 | 1.00 | 1.00 | 1.00 | 85.0 | 18.0 |
| 5.0 | 100.0 | 1.00 | 1.00 | 1.00 | 95.0 | 20.0 |
| 5.0 | 200.0 | 1.00 | 1.00 | 1.00 | 195.0 | 40.0 |
| 5.0 | 500.0 | 1.00 | 1.00 | 1.00 | 495.0 | 100.0 |
| 5.0 | 1000.0 | 0.00 | 1.00 | 1.00 | 995.0 | 200.0 |

TABLE 10

| $VO_2$ ml/kg/min | VI ml/kg/min | $FiO_2$ | $FmO_2$ | $FmO_2 \div FiO_2$ | K ml/kg/min | $VI \div VO_2$ | Tolerance |
|---|---|---|---|---|---|---|---|
| 5.0 | 200.0 | 0.21 | 0.19 | 0.90 | 195.0 | 40.0 | 10% |
| 5.0 | 200.0 | 0.30 | 0.28 | 0.94 | 195.0 | 40.0 | 10% |
| 5.0 | 80.0 | 0.40 | 0.36 | 0.90 | 75.0 | 16.0 | 10% |
| 5.0 | 60.0 | 0.50 | 0.45 | 0.91 | 55.0 | 12.0 | 10% |
| 5.0 | 40.0 | 0.60 | 0.54 | 0.90 | 35.0 | 8.0 | 10% |
| 5.0 | 30.0 | 0.70 | 0.64 | 0.91 | 25.0 | 6.0 | 10% |
| 5.0 | 20.0 | 0.80 | 0.73 | 0.92 | 15.0 | 4.0 | 10% |
| 5.0 | 20.0 | 0.90 | 0.87 | 0.96 | 15.0 | 4.0 | 10% |
| 5.0 | 6.0 | 1.00 | 1.00 | 1.00 | 1.0 | 0.83 | 10% |

Tables 1–9 illustrate the $FmO_2$ achieved at various inspiratory gas flow rates (VI) assuming an oxygen consumption rate of 5 ml/kg/min. An asterisk in the column labeled $VI/VO_2$ indicates the minimum flow rate of inspiratory gas needed to achieve an $FmO_2$ that is within 10% of the corresponding $FiO_2$. The inspiratory gas corresponding to Table 1 was air (21% oxygen). As seen in Table 1, an inspiratory gas flow rate of 50 ml/kg/min results in the fraction of $O_2$ in the mixed gas (mixture of inspiratory gas and scrubbed exhaled gas) to be about 0.12. Thus, the ratio of $FmO_2$ to $FiO_2$ is about 0.58. To achieve the fraction of oxygen in the mixed gas ($FmO_2$) to be within 10% of the $FiO_2$, a flow rate of inspiratory gas of 200 ml/min is needed.

Tables 2–9 illustrate the flow rate of inspiratory gas required for $FiO_2$ values of 0.3 (30m% oxygen) to 1.0 (pure oxygen). With a higher percentage of oxygen in the inspiratory gas, a lower flow of inspiratory gas is needed to achieve the same ratio of $FmO_2$ to $FiO_2$. For example to achieve an $FmO_2$ value that is within 10% of $FiO_2$, for gas containing 21% oxygen (air) an inspiratory gas flow rate of 200 ml/min is required, whereas for inspiratory gas containing 80% oxygen, a 10 times lower inspiratory gas flow rate (20 ml/kg/min) is required (Table 7). Table 10 presents a composite of inspiratory gas flow rates for various concentrations of oxygen in the inspiratory gas to achieve an $FmO_2$ value that is within 10% of the $FiO_2$ (10% tolerance level). As seen in Table 10, to deliver a desired concentration of oxygen to the patient line 25, one could adjust the inspiratory gas flow keeping the $FiO_2$ constant, or one could adjust the $FiO_2$ keeping the inspiratory gas flow rate constant.

The data presented in these tables illustrates that by using the device of the present invention, inspiratory gas flow rates can be reduced to 6 to 200 ml/kg/min. This compares to an inspiratory gas flow rate of approximately 1000 to 2000 ml/kg/min required with currently available high frequency oscillatory ventilators.

Figure 8:
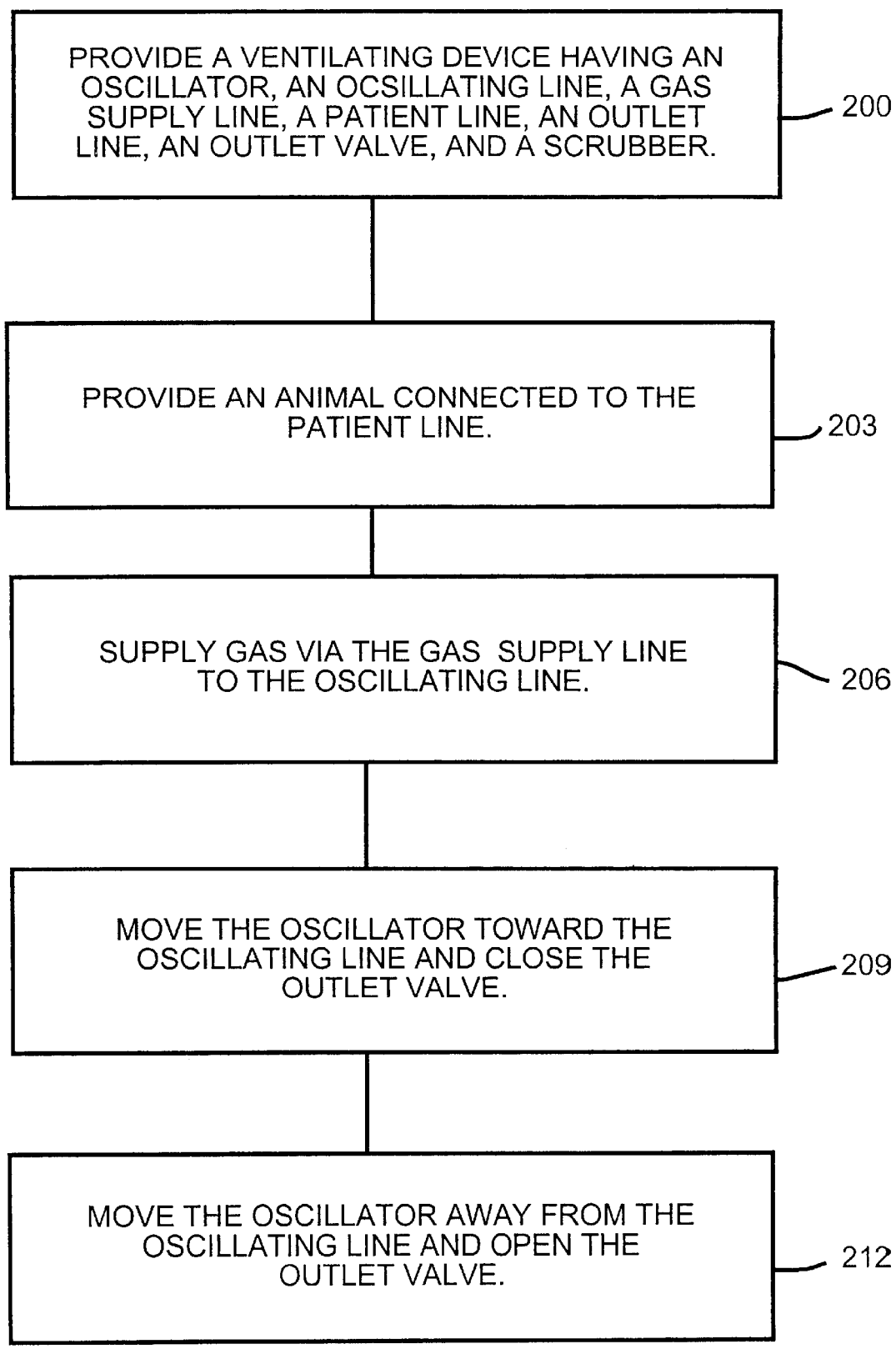
FIG. 8 is a flow chart showing steps of a method according to the present invention.

FIG. 8 shows steps of a method according to the present invention. In the method, a ventilating device, such as the device 10 described above, is provided (step 200). In addition, a patient connected to the patient line is provided (step 203) and gas is supplied with the gas supply line to the oscillating line (step 206). The oscillator is moved toward the oscillating line and the outlet valve is opened (step 209). Then, the oscillator is moved away from the oscillating line and the outlet valve is closed (step 212). Preferably, the gas is supplied to the oscillating line at approximately a constant flow rate.

Devices and methods according to the present invention are more efficient than currently available high frequency oscillating ventilators primarily because the present invention substantially reduces the need for bias flow. This reduction in bias flow enables smaller ventilation systems. It is now clear the device and method of the present invention reduces the volume of bias flow required for safe ventilation. By using the present device, it is believed the volume of inspiratory gas delivered to the ventilator can be reduced from 20,000 to 80,000 ml/min to as little as 20 to 800 ml/min.

Another advantage of the present invention may be to counter the loss of mean lung volume associated with prolonged oscillatory ventilation, which is believed to be a problem with this form of mechanical ventilation. It is currently believed by some that this problem might be intensified by reductions in inspiratory gas flow. One approach to this problem that may counter a tendency to lose mean lung volume and thus preserve lung expansion involves redirection of some or all of the inspiratory gas flow to a small channel adapted to the endotracheal tube to allow delivery of some or all of the bias flow directly to the trachea. While potentially hazardous at high (conventional) inspiratory gas flow rates, it is believed that this would be safe at the lower inspiratory gas flow rates envisioned for this invention. Moreover, it is recognized that there might be some advantage to redirecting some or all of the inspiratory gas flow to the distal trachea (closer to the lungs) even when practicing oscillation using conventional high flow rates of inspiratory gas. Redirection of some or all of the inspiratory gas to the trachea would trap inspiratory gas in the lung during the inspiratory phase of the cycle, and release it to the device 10 at lower pressure during the expiratory phase. This should aid in the expansion of an atelectatic or de-recruited lung.

Although preferred embodiments of the present invention have been described and illustrated herein, the present invention is not limited to such preferred embodiments. Since various changes could be made without departing from the spirit and scope of the invention, it is intended that the foregoing description shall be interpreted as illustrative, and not interpreted in a limiting sense. Furthermore, it is intended that the present invention shall be limited only by the following claims.

What is claimed is:

1. A ventilating device, comprising:
   an oscillator;
   an oscillating line having a first end and a second end, the first end is in sealing relationship with the oscillator;
   a gas supply line connected to the oscillating line and connected to a supply of gas;
   a patient line connected to the second end of the oscillating line;
   an outlet valve in pneumatic communication with the patient line;
   a $CO_2$ scrubber in pneumatic communication with the patient line; and
   a first check valve located in the oscillating line between the oscillator and the second end of the oscillating line.

2. The device of claim 1, further comprising:
   an exhalation line having an inlet connected to the patient line.

3. The device of claim 2, further comprising:
   a second check valve in the exhalation line; and
   wherein the exhalation line has an outlet connected to the oscillating line.

4. The device of claim 3, wherein the $CO_2$ scrubber is located in the exhalation line.

5. The device of claim 1, wherein the outlet valve is connected to the oscillating line.

6. The device of claim 5, wherein the outlet valve is connected to the oscillating line between the oscillator and the first check valve.

7. The device of claim 5, wherein the outlet valve is connected to the oscillating line between the first check valve and the patient line.

8. The device of claim 1 wherein the $CO_2$ scrubber is connected to the second end of the oscillating line.

9. The device of claim 8, wherein the $CO_2$ scrubber is also connected to the patient line.

10. The device of claim 8, wherein the outlet valve is connected to the patient line.

11. The device of claim 8, wherein the outlet valve is connected to the oscillating line.

12. The device of claim 11, wherein the outlet valve is connected to the oscillating line between the $CO_2$ scrubber and the oscillator.

13. The device of claim 1, wherein the outlet valve is caused to release gas for a period of time as the oscillator moves toward the oscillating line.

14. The device of claim 1, wherein the outlet valve is caused to be closed for a period of time as the oscillator moves away from the oscillating line.

15. The device of claim 1, further comprising a bypass line connected to an inlet of the $CO_2$ scrubber.

16. The device of claim 15, wherein the bypass line is also connected to an outlet of the $CO_2$ scrubber.

17. The device of claim 15, wherein the bypass line is also connected to the oscillating line.

18. The device of claim 1, wherein the outlet valve is caused to release gas for a period of time as the oscillator moves away from the oscillating line.

19. The device of claim 1, wherein the outlet valve is caused to be closed for a period of time as the oscillator moves toward the oscillating line.

20. The device of claim 18, wherein the outlet valve comprises an actuator having a first flexible membrane disposed in the oscillating line, a second flexible membrane situated to selectively close an end of the exhalation line, and a pressure communicating line between the first and second membranes.

21. The device of claim 20, further comprising a control pressure line connected to the pressure communicating line.

22. A ventilating device, comprising:
    an oscillator;
    an oscillating line having a first end and a second end, the first end is in sealing relationship with the oscillator;
    a gas supply line connected to the oscillating line and connected to a supply of gas;
    a patient line connected to the second end of the oscillating line;
    an exhalation line connected to the patient line;
    an outlet valve in the exhalation line and operable to release gas from the exhalation line during exhalation, and operable to close during inhalation; and
    a check valve located in the oscillating line between the oscillator and the second end of the oscillating line.

23. The method of claim 22, further comprising moving the oscillator away from the oscillating line and closing the outlet valve.

24. The method of claim 22, wherein the gas is supplied to the oscillating line at approximately a constant flow rate.

25. A method of ventilating, comprising:
    providing a ventilating device having an oscillator, an oscillating line including a first end and a second end, wherein the first end is in sealing relationship with the oscillator, and further having a gas supply line connected to the oscillating line and connected to a supply of gas, a patient line connected to the second end of the oscillating line, an outlet valve in pneumatic communication with the patient line, a $CO_2$ scrubber and a check valve located in the oscillating line between the oscillator and the second end of the oscillating line;
    providing a patient connected to the patient line;
    supplying gas with the gas supply line to the oscillating line;
    moving the oscillator toward the oscillating line; and
    opening the outlet valve.

26. The method of claim 22, wherein the gas includes a therapeutic gas.

27. A ventilating device, comprising:
    an oscillator;
    an oscillating line having a first end and a second end, the oscillating line being in pneumatic communication with the oscillator;
    a patient line connected to the second end of the oscillating line;
    a gas supply line in pneumatic communication with the oscillating line and connected to a supply of gas;
    an outlet valve in pneumatic communication with the patient line;
    a $CO_2$ scrubber in pneumatic communication with the patient line; and
    a first check valve located in the oscillating line.

28. The device of claim 27, further comprising an exhalation line having an inlet connected to the patient line.

29. The device of claim 28, further comprising a second check valve located in the exhalation line, and wherein an outlet of the exhalation line is connected to the oscillating line between the oscillator and the first check valve.

30. The device of claim 28, wherein the outlet valve is caused to release gas for a period of time as the oscillator moves toward the oscillating line.

31. The device of claim 28, wherein the outlet valve is caused to close for a period of time as the oscillator moves away from the oscillating line.

32. The device of claim 28, further comprising a bypass line having an end in pneumatic communication with the oscillating line and another end in pneumatic communication with the exhalation line and operable to provide a pathway bypassing the scrubber.

33. The device of claim 28, wherein the outlet valve is connected to the patient line.

34. The device of claim 27, further comprising a bypass line having an end connected to an inlet of the $CO_2$ scrubber.

35. The device of claim 34, wherein the bypass line has another end connected to an outlet of the $CO_2$ scrubber.

36. A ventilating device, comprising:

an oscillator;

an oscillating line having a first end and a second end, the first end is in pneumatic communication with the oscillator;

a gas supply line in pneumatic communication with the oscillating line and connected to a supply of gas;

a patient line connected to the second end of the oscillating line;

an outlet valve in pneumatic communication with the patient line;

a $CO_2$ scrubber in pneumatic communication with the patient line; and a first check valve located between the patient line and a patient.

37. The device of claim 36, wherein the $CO_2$ scrubber is located between a patient and the patient line.

38. The device of claim 37, wherein the $CO_2$ scrubber is located in a line that provides gas to a patient.

39. The device of claim 37, further comprising a return line and a check valve located to allow unidirectional flow through the scrubber.

40. The device of claim 31, wherein the scrubber is located in a line that provides gas to a patient.

41. The device of claim 39, wherein the scrubber is located in the return line.

* * * * *